(12) United States Patent
Sodo

(10) Patent No.: US 8,425,475 B2
(45) Date of Patent: Apr. 23, 2013

(54) SANITARY APPARATUS FOR INTESTINAL CLEANSING

(75) Inventor: Diego Sodo, Naples (IT)

(73) Assignee: Iniziativa centro sud srl, Naples (IT)

( * ) Notice: Subject to any disclaimer, the term of this patent is extended or adjusted under 35 U.S.C. 154(b) by 199 days.

(21) Appl. No.: 12/979,805

(22) Filed: Dec. 28, 2010

(65) Prior Publication Data
US 2012/0165758 A1    Jun. 28, 2012

(51) Int. Cl.
| A61M 31/00 | (2006.01) |
| A47K 3/20 | (2006.01) |
| A47K 4/00 | (2006.01) |
| A47K 3/022 | (2006.01) |
| A47K 3/26 | (2006.01) |
| E03D 9/08 | (2006.01) |
| A61H 35/00 | (2006.01) |

(52) U.S. Cl.
USPC ............... 604/275; 604/279; 4/420.4; 4/443; 4/448

(58) Field of Classification Search ............. 604/275, 604/276, 279; 4/420.1–420.4, 443–448
See application file for complete search history.

(56) References Cited

U.S. PATENT DOCUMENTS

| 1,940,210 | A | | 12/1933 | Frederick |
| 2,583,298 | A | | 1/1952 | Kowan |
| 2,758,600 | A | | 12/1953 | Vrana et al. |
| 2,954,046 | A | | 9/1960 | Lloyd |
| 3,937,224 | A | * | 2/1976 | Uecker ............... 604/101.05 |
| 4,205,402 | A | * | 6/1980 | Miller ............... 4/448 |
| 4,284,078 | A | | 8/1981 | Pace |
| 4,326,308 | A | * | 4/1982 | Silver ............... 4/420.3 |
| 5,411,494 | A | * | 5/1995 | Rodriguez ............... 604/290 |
| 5,657,954 | A | * | 8/1997 | Emery et al. ............... 248/221.12 |
| 5,946,741 | A | | 9/1999 | Moon |
| 6,478,782 | B1 | | 11/2002 | Wada |
| 2004/0047052 | A1 | | 3/2004 | Zadro |
| 2007/0213668 | A1 | | 9/2007 | Spitz |

FOREIGN PATENT DOCUMENTS
| EP | 1240911 A1 | 9/2002 |
| EP | 1579880 A1 | 9/2005 |

OTHER PUBLICATIONS

Extended European Search Report, dated Jun. 7, 2011, from corresponding EP application.

* cited by examiner

*Primary Examiner* — Bhisma Mehta
(74) *Attorney, Agent, or Firm* — Young & Thompson

(57) ABSTRACT

A sanitary apparatus for intestinal cleansing to be attached to a water faucet (R), comprises a faucet filter (2), a quick coupling (3) connectable to the faucet filter (2) and containing a pressure-relief device. A spiral hose (4) connects the pressure-relief device to a series of devices situated in a rectilinear tube section (16), the series of devices including a temperature control device (5), a flow regulator (6), a metering device (7), a check valve (13) and a rectal nozzle (14) in an end section of the sanitary apparatus. Said end section comprises a semirigid tube (9, 12) sustained by a fixing removable support (10) including a base plate (19) provided with at least a sucker (21) in its lower part, and with U bolt-shaped members (24) clamping the semirigid tube (9, 12) in its upper part.

5 Claims, 5 Drawing Sheets

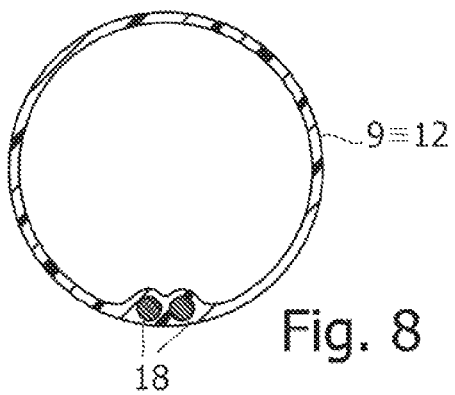
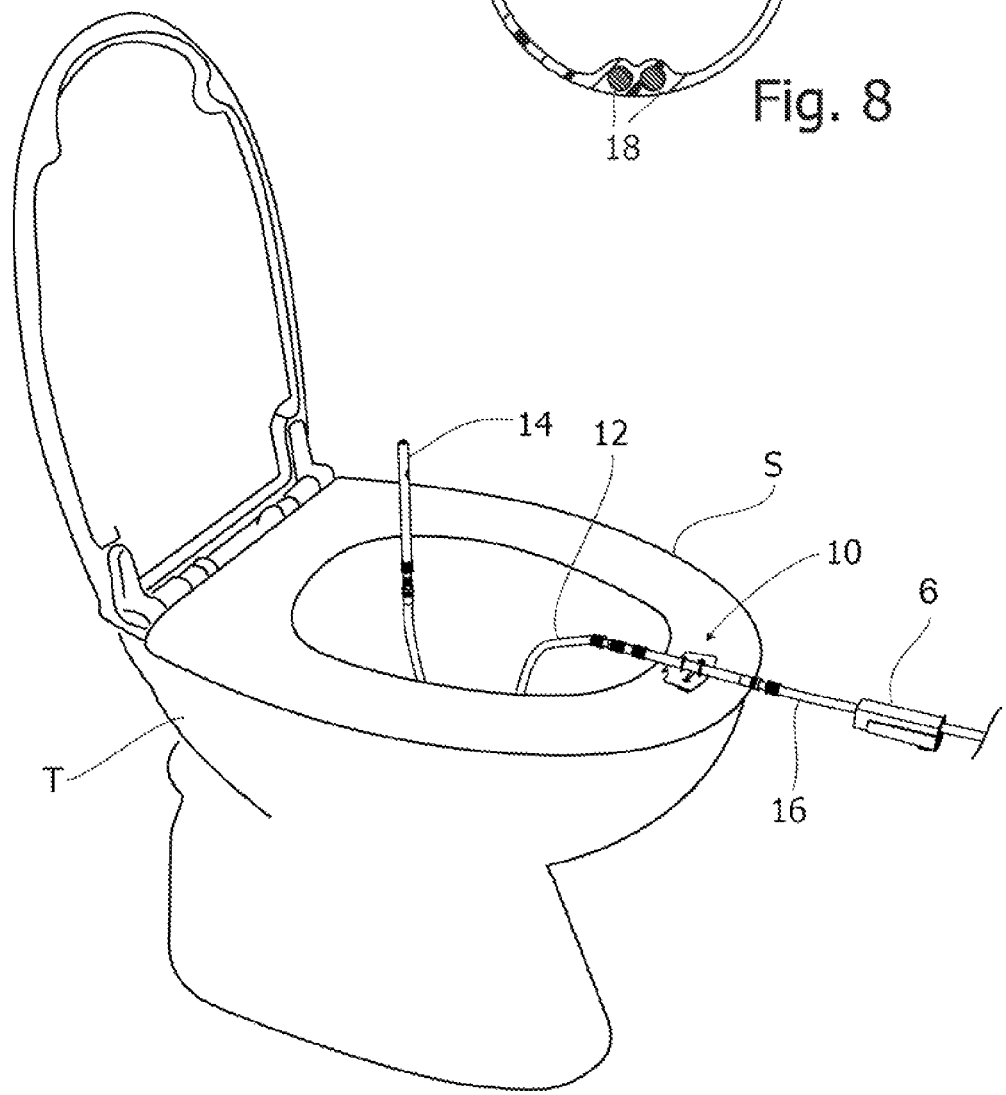
Fig. 8
Fig. 9

SANITARY APPARATUS FOR INTESTINAL CLEANSING

BACKGROUND OF THE INVENTION

1. Field of the Invention

The present invention relates to a sanitary apparatus for intestinal cleansing to be attached to a water faucet. The apparatus can be used sitting on a toilet bowl.

2. Description of Related Art

In the prior art, for example in U.S. Pat. No. 1,940,210, there is an apparatus comprising a faucet fitting integral with means for regulating the pressure and means for metering a medication to be diluted by water from the faucet, and further a tubing provided with a nozzle having a cut-off valve.

U.S. Pat. No. 2,954,046 deals with the problem of the excessively increased water temperature and provides a device adapted to interrupt in this case the flow of water between a faucet and a nozzle.

U.S. Pat. No. 5,946,741 develops above all arrangements of the terminal section of a tubing near a nozzle for the employment thereof, including a manual clamping device to modify the flow rate. It discloses mainly a base plate to rest removably over the bowl and a particular shape of nozzle that is comfortable and does not damage an user.

U.S. Pat. No. 4,284,078 relates to an attachment to a water faucet in order that fresh water may be conveniently dispensed for specific uses such as dental hygiene, bath spray, water enema and vaginal douche. The attachment includes an adapter at one end of a flexible hose for attachment to a faucet, and various interchangeable adapters attachable to the other end of the hose. The first adapter includes a valve for selectively by-passing the attachment so as to allow the obtaining of water directly from the faucet.

EP 1 579 880 discloses a medical apparatus for self-irrigation treatments, to be fitted between a toilet seat and a toilet bowl, the medical apparatus comprising a disposable irrigation tube to be connected to a pressurised water source by means of a water supply line connected to a faucet of a sanitary apparatus like a washbasin or bidet. The medical apparatus comprises a support frame for the irrigation tube, said support frame having a shaped central portion to transversally extend inside the toilet bowl, and two side arms to be locked between a seat and the toilet bowl. A water flow duct extends from a side arm along the support frame, to an upwardly facing pipe fitting for the sealed connection to the irrigation tube. The medical apparatus further comprises two automatic discharge valves, the one connected to said water flow duct, and the other provided in a pressure control unit further including a pressure regulator, a pressure gauge, and a pushbutton tap for opening and closing the water flow.

As one can note from above mentioned, EP 1 579 880 describes a very complex apparatus, which, among the other, has a drawback of the support frame positioned inside the toilet bowl in the evacuation zone. It should be understood that after the intestinal cleansing such a support frame must be suitably cleaned and sanitised, in order to be used again safely.

EP 1 240 911 discloses an apparatus for intestinal cleansing, comprising a seat for a toilet bowl, having in its rear side a feed duct for feeding a cleansing fluid. The feeding duct passes through the hinge between seat and bowl cover and ends with a disposable nozzle.

The apparatus according to EP 1 240 911 needs a particular kind of seat to be positioned instead of that normally in use on the toilet bowl and then it is uncomfortable and does not predispose the user to the operation of intestinal cleansing in the best way.

In the prior art there are also other complex apparatuses, requiring an electrical power and combining several of the above functions. Such complex electrical apparatuses would not be considered by the person skilled in the field for obtaining a combined apparatus.

By examining the subject matter of the above mentioned patents the skilled person would obtain a combined apparatus comprising a single attachment to a faucet, pressure regulating means and metering means, and a separated device against the temperature increase and a manual clamping device for changing the flow rate, and further a supporting base plate and a cut-off valve. Above all, in the cleansing apparatuses mentioned the support on the toilet bowl of the portion of the apparatus near the end tubing implies substantial modifications of the seat and even its substitution. Further, the end section comprising the disposable nozzle has a predetermined position in the apparatus and this forces the user to comply to that position and not vice versa.

SUMMARY OF THE INVENTION

An object of the present invention is to separate the functions relating to attachment, pressure relief and substance metering, by giving them to single devices being independent one from another.

Another object of the invention is to increase the current functions in an apparatus for intestinal cleansing, by adding a used water filtering.

Yet another object of the invention is to provide a quick coupling to the pipe system.

A further object of the invention is to provide in the apparatus tube sections of different kinds able to comply with the different functions like comfortably moving and positioning as desired.

Yet another object is to provide the apparatus with supporting means being steady and removable in the same time.

Finally, an object of the invention is to combine a series of improvements that make better the functions of the apparatuses already known.

Furthermore, with regard to said apparatuses, an object is to provide a sanitary apparatus that does not request any change to the seat of a toilet bowl.

Another important object is to manufacture a sanitary apparatus whose end section with disposable nozzle has no predetermined position and does not force the user to assume uncomfortable postures.

These and other objects of the invention are achieved by a sanitary apparatus for intestinal cleansing as defined in claim 1 and in the claims depending on it.

BRIEF DESCRIPTION OF THE DRAWINGS

Further features and advantages of the present invention will appear mostly clear from the indicative and therefore not limiting description of a preferred and not excluding embodiment thereof, as illustrated in the enclosed drawing in which:

FIG. 8 is an enlarged cross-sectioned view of a semirigid tube of the sanitary apparatus according to the present invention; and FIG. 9 is a fragmentary perspective view of the sanitary apparatus according to the invention as applied on a toilet bowl.

DESCRIPTION OF THE PREFERRED EMBODIMENT

Figure 1:
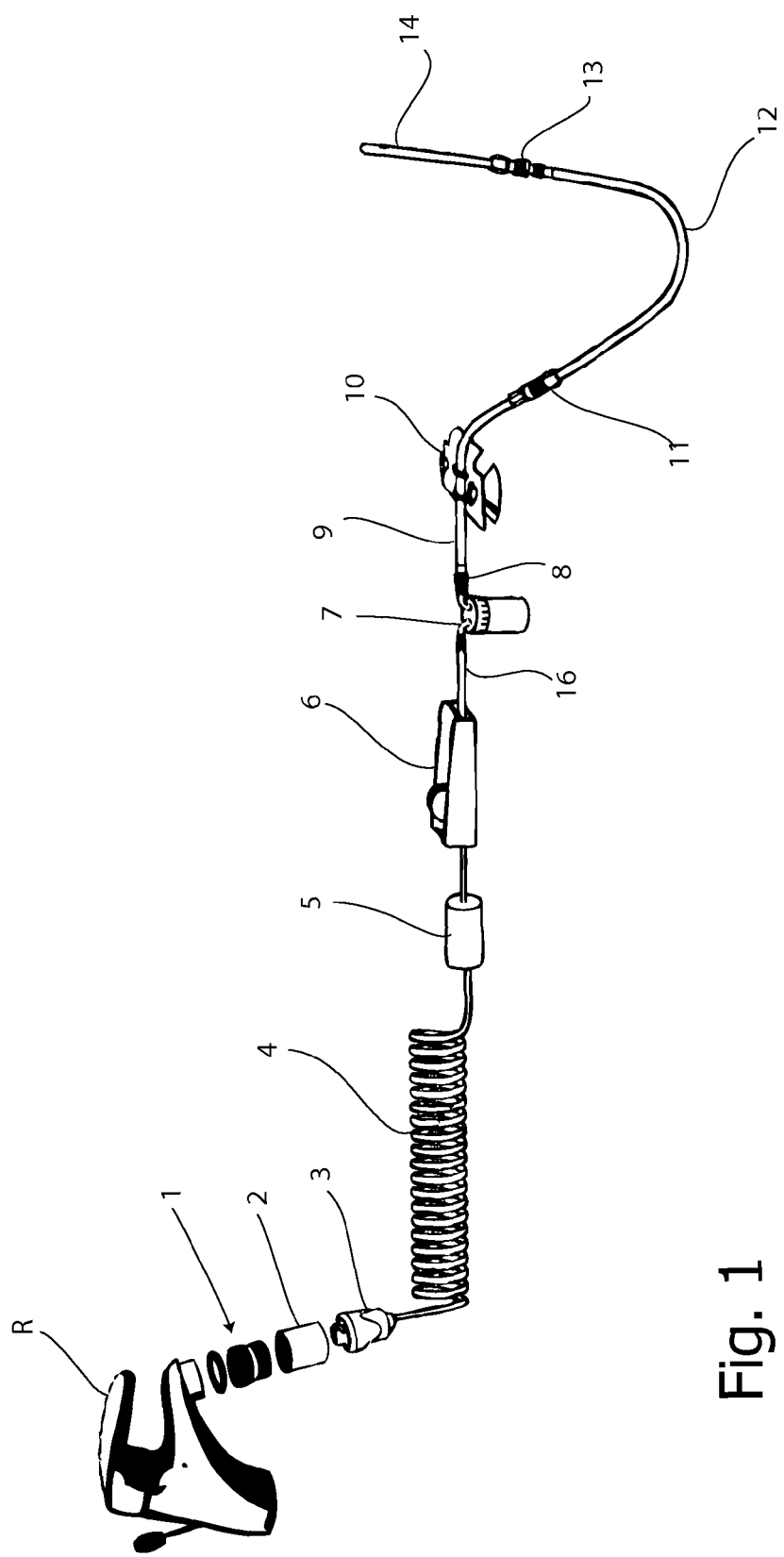
FIG. 1 is a general diagrammatic perspective view of a sanitary apparatus for intestinal cleansing according to the present invention.

With reference to the diagrammatic perspective view in FIG. 1, indicated as R is a faucet, as 1 an adapter with seal, as 2 a filter, as 3 a quick coupling, as 4 a spiral hose, as 5 a temperature control device, as 6 a flow regulator, as 7 a metering device, as 8 a pipe fitting, as 9 a first semirigid tube section, as 10 a tube fixing removable support, as 11 a pipe fitting, as 12 a second semirigid tube section, as 13 a check valve and as 14 a rectal nozzle.

The apparatus according to the invention comprises such a filter 2 that can fit in the faucet R and in the quick coupling 3 in the opposite ends thereof. Both the filter 2 and the quick coupling 3 can be arranged and operate like those described in the Italian patent N. 1325538 of the same Applicant.

The filter 2 has to be mounted to the faucet R, as it replaces the existing filter on the faucet. The filter 2 can be kept permanently on the faucet since the filter 2 allows the faucet to be used normally, also acting as an aerator. The filter 2 is complete of seals and can be adapted to different kinds of faucet by means of the adapter 1 having both an internal and external thread.

A pressure-relief device is provided in the quick coupling 3 that is connected directly to the filter 2. The pressure-relief device consists of a safety valve having a spring-charged shutter (not shown in detail). When a force acting on the shutter due to the faucet water pressure overcomes the counteracting force of the spring, the shutter opens and allows an automatic water discharge in the washbasin. In this way, the flow will never be at a too high pressure. It is suitable that the pressure-relief device may be manually adjusted by the user, for example by a fine screw regulation acting on the spring and being able to modify the counteracting force thereof. In this way the water flow rate can be changed as desired, preferably in a run signalled by clicks of the fine regulation. An advantage of the flow rate regulation will be evident below in relation with the metering device 7.

The spiral hose 4 is inserted in the quick coupling 3 and is long enough (for example 3.0 m) to allow the sanitary apparatus to be connected to a bidet or washbasin and used, for example, on a toilet bowl.

The temperature control device 5 of every type known permits the water passage to be cut-off if the water temperature is greater than a predetermined threshold (about 38 Celsius degrees).

The flow regulator 6 can be for example of the so called roller type for I.V. that easily permits the water flow to be increased or decreased without acting directly on the faucet. As better shown in FIGS. 2 and 3, that are an enlarged fragmentary perspective view of the sanitary apparatus in FIG. 1 and an exploded view thereof respectively, the flow regulator 6 has an housing 15 through which a rectilinear section 16 in continuation of the spiral hose 4 passes. A milled roller 17 is pivoted in width decreasing grooves made in opposed side walls of the housing 15, so that the rectilinear section 16 is gradually blocked when the milled roller 17 is moved from one end to the other of the housing 15.

The metering device 7, also this one being of any type known, allows the water from the faucet R to be mixed with a detergent or medicinal substance. Some of these substances need accurate dosage, i.e. the substance must arrive to the user in a precise proportion with respect to water flow rate. A fine regulation of the flow rate obtained by the pressure-relief device allows the amount of substance added to the water flow to be kept constant, but also variable according to needs.

A first section 9 of semirigid tube is connected to the metering device 7 by means of a pipe fitting 8. The first tube section 9 of a length e.g. of about 10-15 cm can be made of PVC including at least a metal core. As shown in FIG. 8, which is an enlarged cross-sectioned view of a semirigid tube of the sanitary apparatus according to the present invention, the tube section 9 is provided, by way of example, with two near parallel copper wires 18 embedded in the wall of the semirigid tube, and can be shaped according to the position as desired by the user of the apparatus.

The fixing removable support 10 is better illustrated in FIGS. 4 to 7, which are plan views from the top and from the bottom, side view and perspective view thereof. The fixing removable support 10 comprises a base plate 19 shaped, if any, with a bent portion 20 that matches the profile of the seat of the toilet bowl. The seat is indicated as S in FIG. 9, which is a fragmentary perspective view of the sanitary apparatus according to the invention as applied on a toilet bowl T. The base plate 19 is provided in its lower part with a pair of suckers 21, each of which has a head 22 blocked on the base plate 19 in an elongated slot 23. The elongated slot 23 is shaped with a decreasing width from the middle thereof toward both ends so that each sucker head 22 is inserted in the middle of the elongated slot 23 and blocked in an end thereof.

The semirigid tube section 9 is retained by friction on the base plate 19 by two U bolt-shaped members 24 made in the upper part of the base plate 19. The semirigid tube section 9 passes under the two U bolt-shaped members 24.

Small pins indicated generally as 25, acting as spacers, are provided in the lower part of the base plate 19.

By virtue of its shape, the removable support 10 can be mounted in an adjustable manner as desired on the seat S of the toilet bowl T or on the same toilet bowl. The position of the removable support 10 may be chosen according to user's needs and preferences; for example, the position can be frontal, so that the removable support 10 is situated between the user's legs. In this way the section 9 of semirigid tube remains steady, in the desired position, throughout the use of the apparatus.

Figure 3:
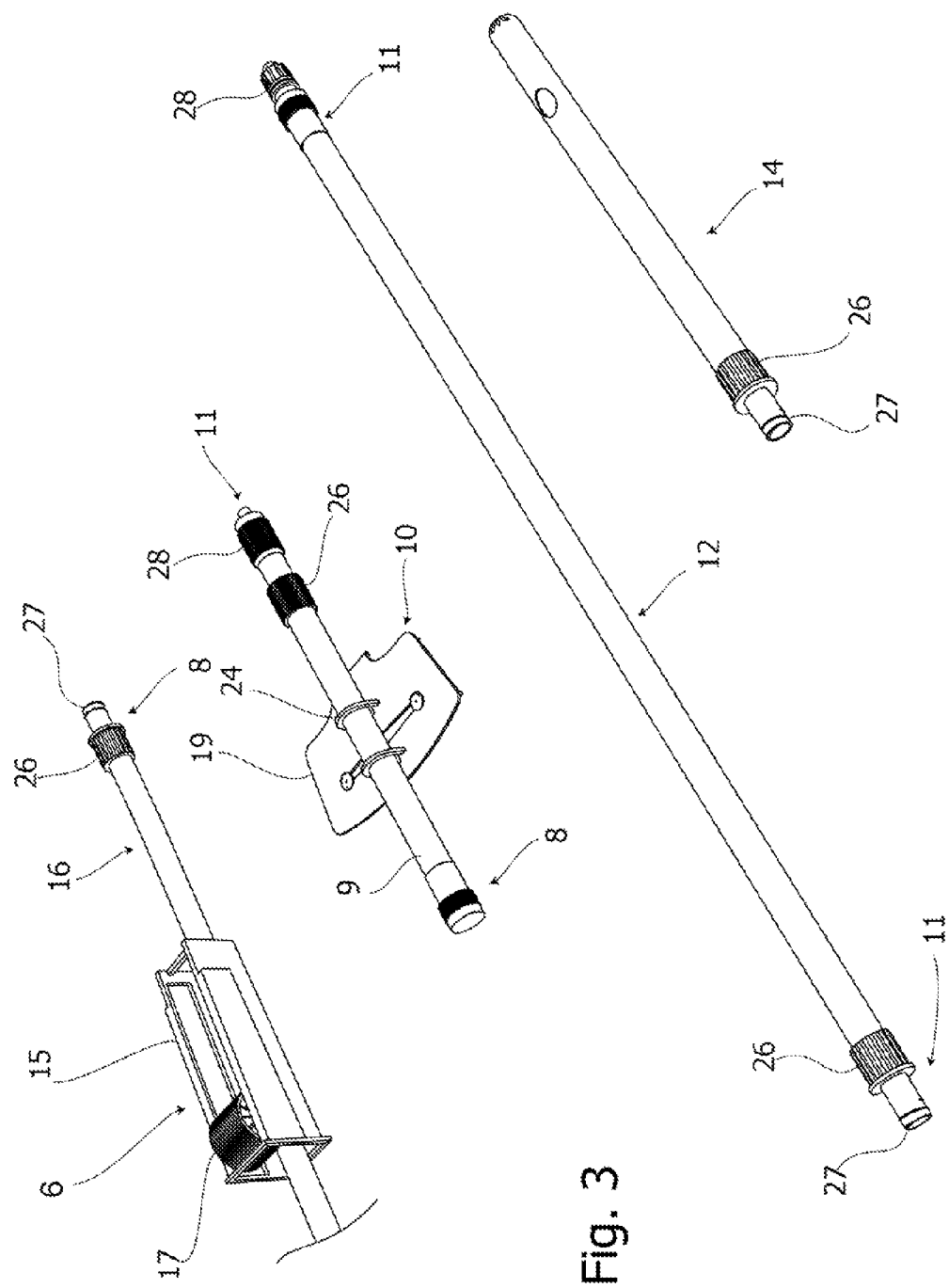
FIG. 3, similar to that in FIG. 2, is an exploded view.
Figure 4:
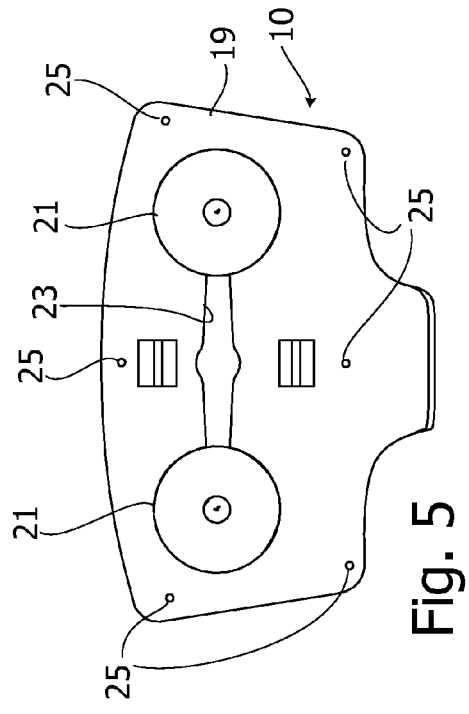
FIGS. 4 to 7 are plan views from the top and from the bottom, side view and perspective view of a removable support for fixing the sanitary apparatus according to the present invention.
Figure 5:
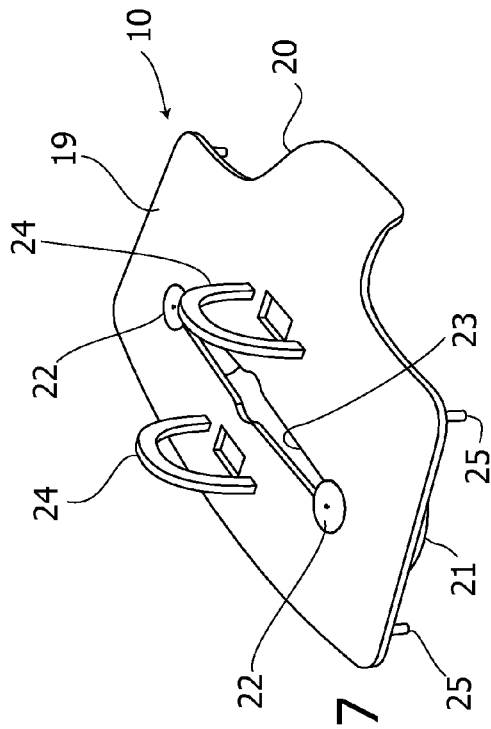
Figure 6:
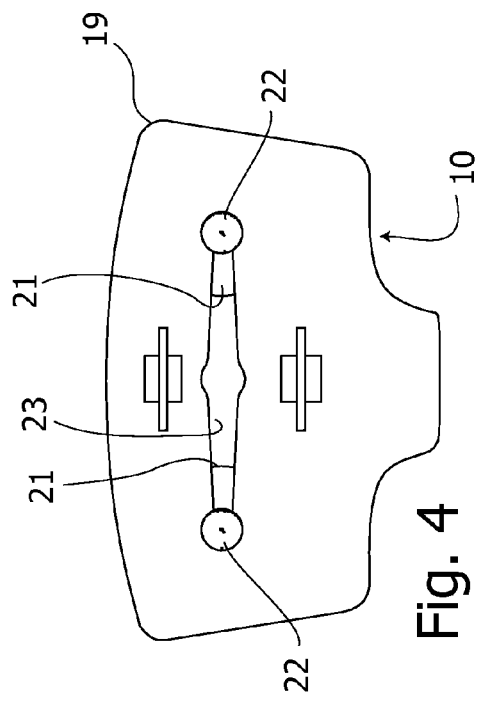
Figure 7:
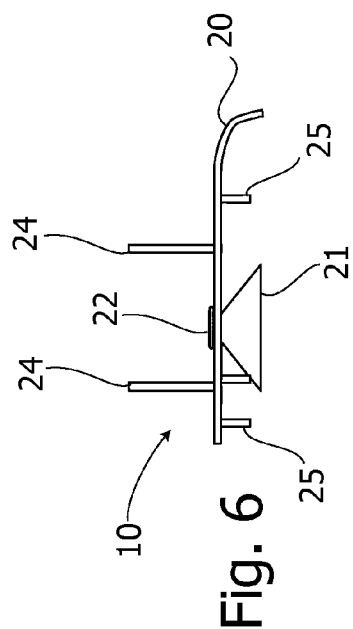

A threaded pipe fitting 11, as shown in FIG. 3, or a snap pipe fitting, allows a second section 12 of semirigid tube to be released. In this way the second section 12 of semirigid tube, that gets dirty in the use of the apparatus, can be washed simply and practically. Also the section 12 of the semirigid tube can be made of PVC with at least a metal core, as shown in FIG. 8. Thanks to the wires 18, the tube section 12 may be shaped according to the position desired by the user of the apparatus. Then, the tube is able to adapt to the different needs of the users and permits the use of the apparatus comfortably and without any trouble.

Figure 2:
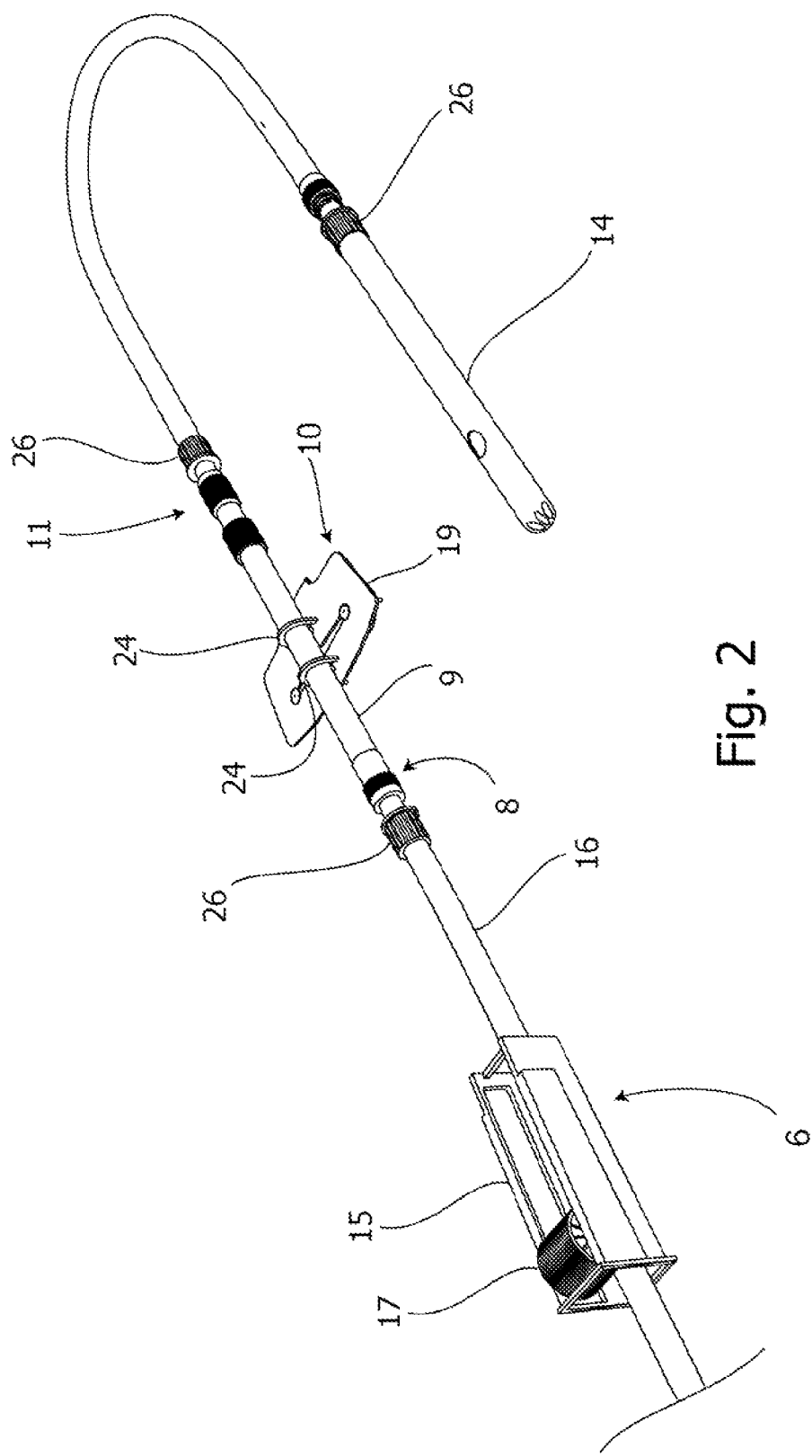
FIG. 2 is an enlarged fragmentary perspective view of the sanitary apparatus in FIG. 1.

Generally indicated in FIGS. 2 and 3 as 26 are milled engrossments in a first tube that make comfortable a tube grip when a sleeve portion 28 being part of a pipe fitting 8 or 11 of a second adjacent tube is screwed on or unscrewed from a threaded portion 27 of the first tube.

The check valve 13 (not shown in FIGS. 2 and 3) is situated at the end of the section 12 of the semirigid tube and assures that evacuated material does not return in circulation of the sanitary apparatus.

A rectal nozzle 14 is connected to the check valve 13. The rectal nozzle 14, which is provided in a not sterile package, is connected to the check valve 13 thanks to a threaded pipe fitting 11 that permits the detachment thereof after the use.

The metering device 7, which may be alternatively provided in a section 9 or 12 of semirigid tube, receives internally a gel, for example glycerine, a tablet or a liquid of a substance suitable to improve the intestinal cleansing of the tube. The cleansing substance, which could also be a granular material or a powder, flows then in the rectal nozzle 14 for the intestinal cleansing. Near the metering device 7, the tube section may be transparent to permit the user to see when the substance to be diluted is finished.

For its use the apparatus according to the invention is connected to the faucet R, after replacing the existing filter in the faucet with the apparatus filter 2 and the addition, if any, of the adapter 1. Then, the quick coupling 3 is connected to the filter 2, and the fixing removable support is mounted through its suckers 21 on the seat S of the toilet bowl T or on the same bowl.

The flow regulator 6 situated at the end of the spiral hose 4 is closed, and the faucet R is opened moderately. The pressure-relief device inside the quick coupling 3 will discharge automatically all the water directly in the washbasin (o bidet), as the passage through the apparatus has been closed.

When the user sits on the toilet bowl T, he/she attends to comfortably insert the rectal nozzle 14. Then, yet remaining seated, the user gradually opens the water passage by the flow regulator 6 to the desired pressure for starting the cleansing. The pressure-relief device assures that the flow is never in excess, also if the flow regulator 6 is completely open.

When the cleansing is finished, the user reduces to the minimum the water passage by the flow regulator 6 and, after closing the faucet R, detaches the quick coupling 3 from the filter 2 and the removable support 10 from the seat of the toilet bowl. In order to wash the section 12 of semirigid tube that has got dirty in its use, he/she detaches the pipe fitting 11 and washes the end part of the tube under the faucet. After the use, the rectal nozzle 14 shall be unscrewed and not reused for other cleansing.

The advantages of the apparatus according to the invention are many.

The pressure-relief device is situated inside the quick coupling and automatically adjusts the water pressure. Then, it is not necessary to care for the water pressure of the faucet during the operation because the water will be automatically discharged when the pressure becomes excessive. Such a pressure-relief device can be adjusted in its manufacture for permitting an appropriate pressure, and after by adjusting the counteracting force of the spring of the pressure-relief device. This regulation of the flow rate can be used for obtaining a precise dosage.

The flow regulator is positioned frontally, between the user's legs, and this makes easy the flow regulation.

The removable support has an immediate universal installation (adapted to any kind of shape or size of the toilet bowl) thanks to two suckers. The removable support is provided with tube clamp in the form of the U bolt-shaped members 24, permitting the length of the end part of the tube to be adjusted.

The semirigid tube can be shaped to match the user's needs without obliging the user to take forced and uncomfortable postures like in the existing models in which the position of the rectal nozzle is generally fixed. The semirigid tube may be made of flexible plastics.

The end part of the semirigid tube can be detached so that the apparatus can be accurately washed, stored, and reused very safely.

The filter that permits the attachment of the apparatus to the faucet, can remain attached to the faucet also after the use of the apparatus, as the filter, which filters and aerates the water, allows the normal use of the faucet. The check valve avoids the recirculation and the stagnation of bacteria inside the apparatus.

The temperature control device closes the water passage when the temperature of the water overcomes a predetermined threshold.

The components of the sanitary apparatus have been described only diagrammatically, because they can be chosen suitably, provided that they do not depart from the scope of the enclosed claims.

What is claimed is:

1. A sanitary apparatus for intestinal cleansing to be attached to a water faucet, comprising a faucet filter, a quick coupling connectable to the faucet filter and containing a pressure-relief device, a spiral hose that connects the pressure-relief device to a series of devices situated in a rectilinear tube section, the series of devices including a temperature control device, a flow regulator, a metering device, a check valve and a rectal nozzle in an end section of the sanitary apparatus, said end section comprising a semirigid tube sustained by a fixing removable support including a base plate, wherein the base plate is provided with a pair of suckers constructed and arranged to mount the fixing removable support on a seat of a toilet bowl in a frontal position between a user's legs.

2. The apparatus according to claim 1, wherein the semirigid tube is a tube made of flexible plastics having a wall in which a core formed of at least a wire is embedded.

3. The apparatus according to claim 1, wherein the base plate is provided in an upper part of the base plate with U bolt-shaped members clamping said semirigid tube, the base plate having an elongated slot retaining said pair of suckers provided with sucker heads, the elongated slot being shaped with a decreasing width from the middle thereof toward both ends so that each sucker head is inserted in the middle of the elongated slot and blocked in an end thereof.

4. The apparatus according to claim 1, wherein said base plate is provided in a lower part of the base plate with small pins acting as spacers.

5. The apparatus according to claim 1, wherein said base plate is shaped with a bent portion that matches a profile of the seat of the toilet bowl.

* * * * *